United States Patent [19]

Kurimura et al.

[11] Patent Number: 4,807,984
[45] Date of Patent: Feb. 28, 1989

[54] APPARATUS AND METHOD FOR SPECIMEN INSPECTION

[75] Inventors: Masaaki Kurimura, Naka; Ryohei Yabe; Isao Shindo, both of Katsuta, all of Japan

[73] Assignee: Hitachi, Ltd., Tokyo, Japan

[21] Appl. No.: 13,799

[22] Filed: Feb. 12, 1987

[30] Foreign Application Priority Data

Feb. 18, 1986 [JP] Japan .................................. 61-33371

[51] Int. Cl.$^4$ ............................................ G02B 21/24
[52] U.S. Cl. ..................................... 350/529; 350/531
[58] Field of Search ................................ 350/524–533; 269/21; 279/3; 250/491.1; 414/222–226; 271/902

[56] References Cited

U.S. PATENT DOCUMENTS

| | | | |
|---|---|---|---|
| 2,549,254 | 4/1951 | Smyth | 269/21 |
| 3,499,714 | 3/1970 | Schellenberg | 269/21 |
| 3,538,883 | 11/1970 | Polin | 279/3 |
| 3,816,700 | 6/1974 | Weiner et al. | 269/21 |
| 3,851,972 | 12/1974 | Smith et al. | 350/529 |
| 4,367,915 | 1/1983 | Georges | 350/530 |
| 4,488,717 | 12/1984 | Sheck | 414/222 |
| 4,528,159 | 7/1985 | Liston | 356/244 |
| 4,538,885 | 9/1985 | Graham et al. | 350/529 |

FOREIGN PATENT DOCUMENTS

| | | | |
|---|---|---|---|
| 14582 | 1/1984 | Japan | 414/222 |
| 284353 | 12/1986 | Japan | 414/222 |

Primary Examiner—John K. Corbin
Assistant Examiner—Martin Lerner
Attorney, Agent, or Firm—Fay, Sharpe, Beall, Fagan, Minnich & McKee

[57] ABSTRACT

A slide specimen extracted from a cassette at a receiving position is carried to a holding position for waiting by a carrier along a carrying pass. While at the holding position, a previously inspected specimen that has been observed through a microscope is placed on the carrying pass at a specimen replacing position. Thereafter the specimen that has been held at the holding position is carried to the replacing position by the carrier, while at the same time the specimen that has just been placed at the replacing position is moved along the carrying pass by the carrier. The specimen then placed in the replacing position is picked up by a pair of holding arms and carried to an observing position of the microscope. The specimen is retained by vacuum adsorption and by specimen retainers which resiliently hold it by means of springs in contact with the vacuum adsorption surface. In the meantime, the specimen that has already been observed and shifted toward the specimen feeder is moved the rest of the way to the specimen feeder and replaced into the original cassette from which it was extracted. After replacing the specimen, a new specimen is extracted and carried to the holding position as the process is repeated until all of the slide specimens have been observed.

7 Claims, 5 Drawing Sheets

APPARATUS AND METHOD FOR SPECIMEN INSPECTION

BACKGROUND OF THE INVENTION

The present invention relates to an apparatus and method for specimen inspection, and is particularly concerned with an apparatus and a method adapted for observing a slide specimen automatically through a microscope.

In case specimens consisting of a blood smeared on a slide glass are inspected successively through a microscope, a quick focusing of the microscope will be one of the requirements for enhancing a throughput. Thus, for example, U.S. Pat. No. 3,848,962 discloses that a specimen be held by means of vacuum adsorption. In this case, a vacuum adsorption surface of the specimen holder functions as a reference plane, and the specimen is held only by vacuum force so that the surface of the specimen will come in contact with the reference plane. However, when a method for holding the specimen only by vacuum force is applied to an apparatus, air leakage may arise due to presence of a flaw on an adsorption surface of the specimen holder of the microscope, deformation and failure of the slide specimen itself, or incoming of dust. Thus holding a specimen by vacuum cannot be maintained so long as this may often occur. If so, then the slide specimen cannot be measured efficiently in succession.

Meanwhile, an automatic blood image classification apparatus made by Hitachi, Ltd. employs a specimen autoloader system, and in the apparatus, a specimen observed through a microscope is transferred into a receiving cassette disposed counter to a feeding cassette. In this case, however, two kinds of cassettes must be prepared even for one piece of specimen, and hence a comparatively large space is required for installation. It is preferable that specimen containing areas be arranged at one spot only for setting a multiplicity of specimens within a limited space, however, such arrangement may take too much time for replacing the specimen.

SUMMARY OF THE INVENTION

An object of the invention is to provide an inspection apparatus capable of proceeding with observation of specimens under the state wherein the specimens are securely held despite a deterioration of vacuum adsorption performance.

Another object of the invention is to provide a specimen inspection apparatus capable of replacing efficiently a specimen for observation through a microscope.

The inspection apparatus according to the invention is characterized in the following combination. That is, in a specimen inspection apparatus, provided with a holder means for holding a specimen with vacuum adsorption, a microscope for observing the specimen held on the holder means, a means for carrying the specimen to be delivered to the holder means to a position where the specimen is replaced, the combination comprises a new specimen holding arm means within the holder means. A vacuum adsorption surface capable of contacting the surface of a specimen is formed on the specimen holding arm means, and an auxiliary means for bringing the specimen into contact with and withdrawing it from the vacuum adsorption surface is further provided thereon.

In a preferred embodiment of the invention, the auxiliary means is provided with a means for pushing a specimen elastically to the vacuum adsorption surface and another means for detaching the specimen forcibly from the vacuum adsorption surface.

Then, in a further preferred embodiment, it comprises a step for retaining a specimen received from a specimen feeder once at a waiting position, a step for keeping the specimen retained at the waiting position to a specimen replacing position after the previous specimen has been observed and returned onto a carrying pass from a specimen holder of the microscope, a step for holding the specimen kept at the specimen replacing position on the holder and keeping the specimen at an observing position of the microscope.

DETAILED DESCRIPTION OF THE PREFERRED EMBODIMENT

Figure 1:
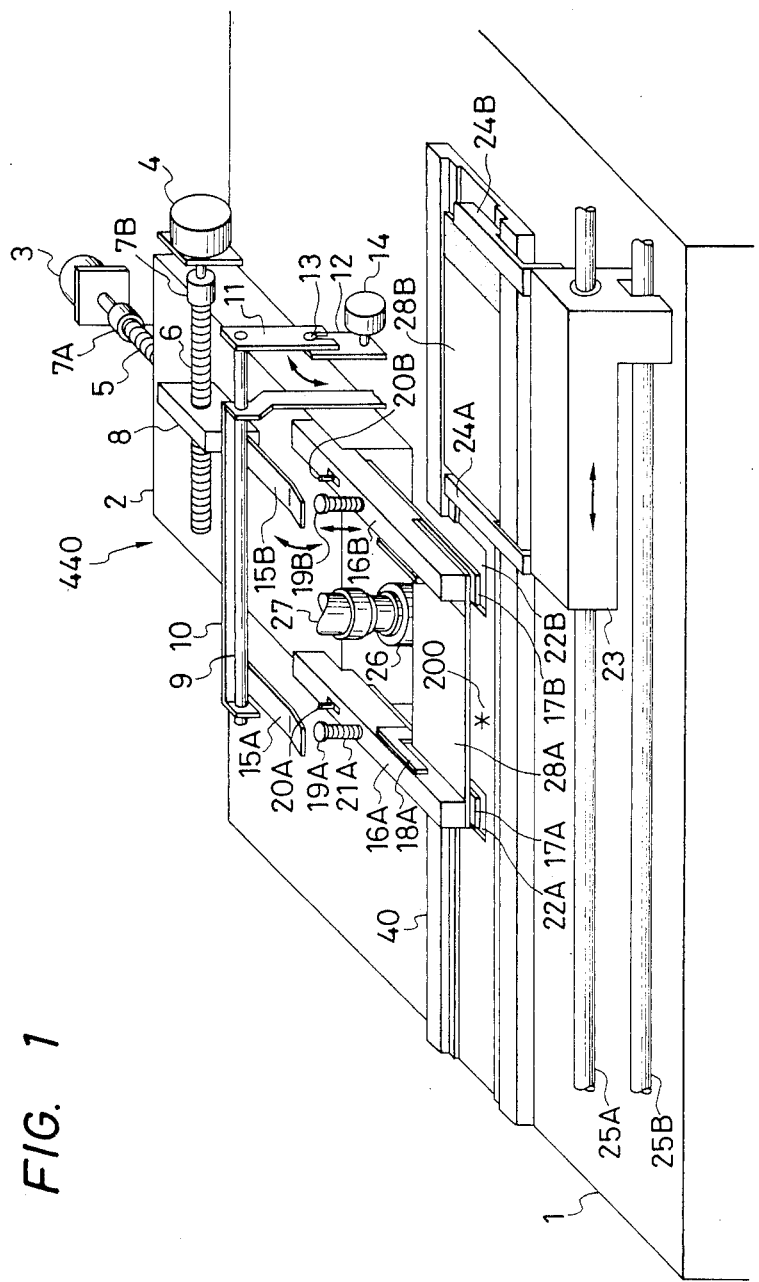
FIG. 1 is a schematic view of the specimen holder of the invention and a blood cell classification apparatus to which the invention is applied.

A construction of the blood cell classification apparatus given in one embodiment of the invention will now be described with reference to FIG. 1, FIG. 2, FIG. 5 and FIG. 6.

The blood cell classification apparatus is provided generally with a specimen feeder 150, a specimen carrier 250, and a measuring apparatus 400 including a microscope. The measuring apparatus 400 is provided with the microscope having lenses 26, 27 and a movable specimen holder 440 having a specimen holding arm 16. The specimen carrier 250 is provided with a carrying pass having a rail 40, and a carrier traveling between a specimen receiving position 100, a specimen replacing position 200 and a specimen holding position 300. The carrier has a moving slider 23 and two feed levers 24A, 24B mounted on the slider 23. The specimen feeder 150 is mounted with a plurality of cassettes 130 containing a multiplicity of slide specimens 28 extractable from a specimen delivery mechanism 120. The specimen delivery mechanism 120 has a construction for moving vertically each cassette 130 selectively and thus positioning the contained specimens to be delivered to the height of the carrying pass. The specimen feeder 150 is also provided with a turntable 110 for positioning each cassette 130 selectively to an area corresponding to the carrying pass.

The specimen holder 440 can be scanned in both directions X and Y so as to place a wide area of on the held slide specimen 28 successively in position for observation through the microscope. The microscope is mounted on a base 1. A pair of holding arms 16A, 16B are fixed on an X—Y stage 2. The X—Y stage 2 is constructed movably in both directions X and Y on the base 1. A female screw 8 is fixed on the X—Y stage 2. A feed screw 5 connected with a pulse motor 3 through a joint 7A and a feed screw 6 connected with a pulse motor 4 through a joint 7B are inserted in stage 2 and female screw 8. Thus, the X—Y stage 2 shifts in the direction X according to a rotation of the pulse motor 4 and also in the direction Y according to a rotation of the pulse motor 3. The X—Y stage 2 is provided with two protuberant holding arms 16A, 16B horizontally extending and parallel to one another. The pair of holding arms 16A, 16B can be positioned on the slide carrying pass on the microscope base 1 and also disposed orthogonally to the slide carrying pass.

The carrier 250 for carrying the slide specimen to a desired position on the carrying pass is provided with two linear shafts 25A, 25B. The slider 23 is mounted on the linear shafts and thus slidable longitudinally thereof. The feed levers 24A, 24B are provided on the slider 23 and are capable of grasping the slide specimen 28 to move it along the rail.

Figure 4:
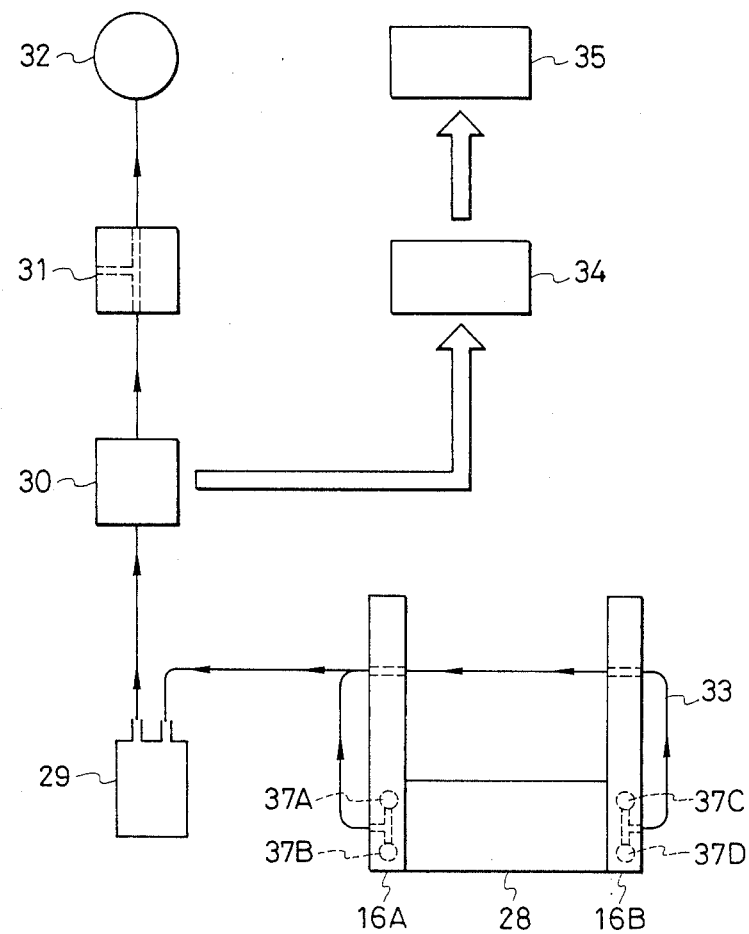
FIG. 4 is a drawing showing a vacuum system of the apparatus in FIG. 1.

A smooth vacuum adsorption surface 50 is formed on the lower surface of both the holding arms 16A, 16B, and openings 37A, 37B, 37C, 37D communicating with a vacuum generator shown in FIG. 4 are formed on the reference plane 50. The surface of the slide specimen 28 comes in contact with the vacuum adsorption surface 50 by vacuum force from the vacuum adsorption holes 37.

Specimen retainers 17A, 17B are mounted movably up and down on the pair of holding arms 16A, 16B respectively. The specimen retainers 17A, 17B are platelike and provided with slider shafts 19A, 19B, guide shafts 20A, 20B and specimen detaching members 18A, 18B. These are movable integrally up and down. Springs 21A, 21B are inserted between upper surfaces of the holding arms 16A, 16B and protrusions 51 of the slider shafts 19A, 19B. The springs 21A, 21B function normally to draw the specimen retainers 17A, 17B upward. The specimen retainers 17A, 17B urge the upper surface of the specimen 28 in contact with the vacuum adsorption surface 50 by the spring force. Accordingly, the specimen can be kept in contact with the vacuum adsorption surface even when the vacuum force is weakened.

The movement of the specimen retainers 17A, 17B is regulated by the guide shafts 20A, 20B inserted in guide holes formed on the arms, 16A, 16B. Thus the specimen retainers move vertically. The holding arms, 16A, 16B hold and release the specimen at the specimen replacing position on the carrying pass. When replacing, a force is applied against the force of springs 21A, 21B by a descending motion of push plates 15A, 15B. As a result the specimen retainers 17A, 17B and the specimen detaching members 18A, 18B descend. The retaining spring force acting on the specimen is released according to the a descent of the specimen retainers. Then, since the specimen 28 is depressed mechanically for descent of the specimen detaching members 18A, 18B, the specimen is forcibly detached from the vacuum adsorption surface. Thus the specimen is released from the holding arms 16A, 16B.

Notches 22A, 22B are formed on the rail 40 of the carrying pass at a predetermined location as shown so that the specimen retainers 17A, 17B may escape downward when upper ends of the shafts 19A, 19B are pused downward by the push plates 15A, 15B.

A mechanism for moving the specimen retainers 17A, 17B downward against the spring force is installed on the base 1. The mechanism includes push plates 15A, 15B, a turning shaft 9 mounted with the push plates, an arm 11 with one end of the turning shaft 9 fixed thereon, another arm 12 provided with a pin 13 engaged with the arm 11, and a rotary solenoid 14 for reciprocating the arm 12. When the rotary solenoid 14 is driven, the turning shaft 9 turns by a predetermined angle to apply a downwardly directed force through the push plates to the shafts 19A, 19B.

As shown in FIG. 4, the openings 37A, 37B, 37C, 37D formed on the holding arms 16A, 16B are connected to an oil tank 29, a vacuum pressure detector 30, a three-way directional control solenoid valve 31 and a vacuum pump 32 by way of a tube 33.

Figure 5:
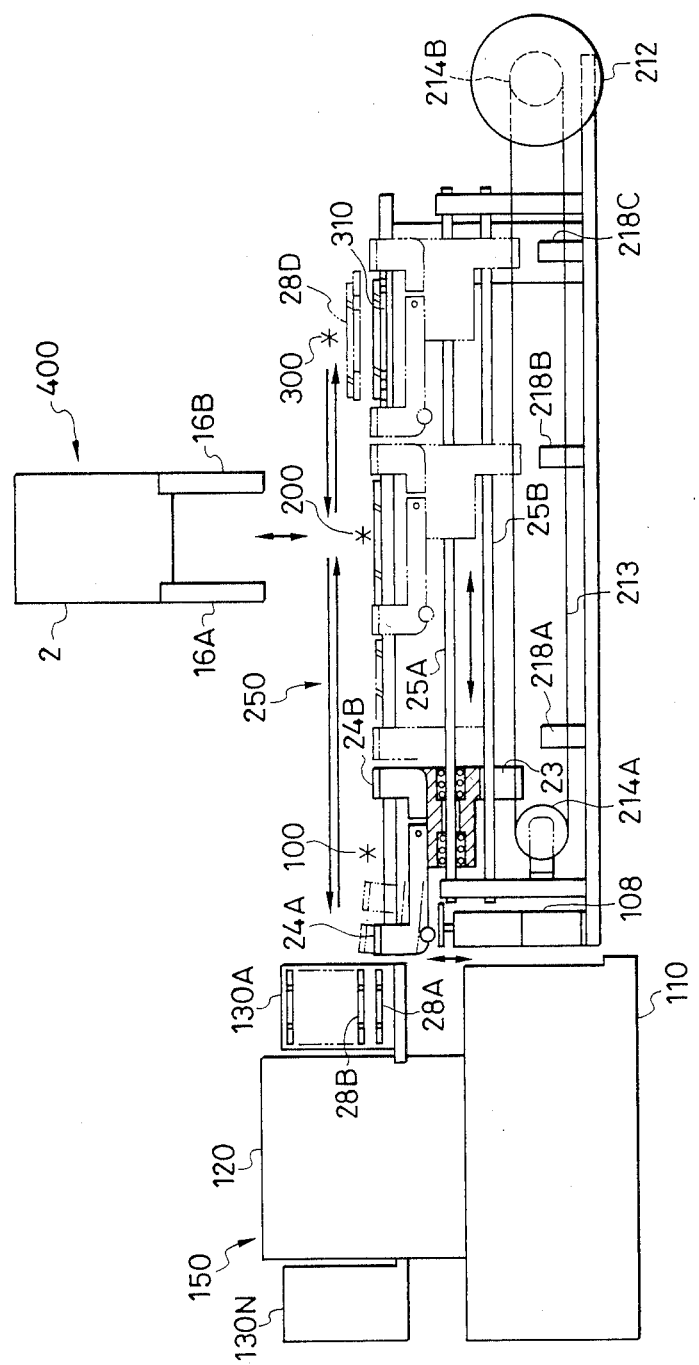
FIG. 5 is a schematic drawing showing a specimen carrier and the blood cell classification apparatus of FIG. 1.
Figure 6:
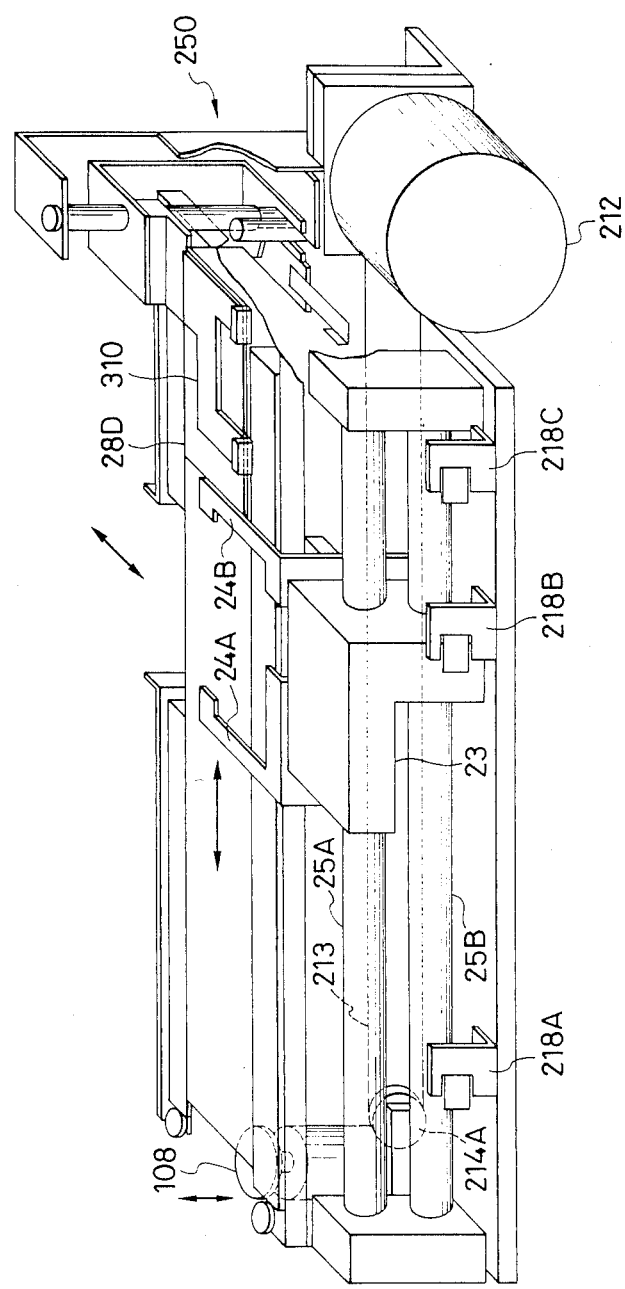
FIG. 6 is a perspective view showing a main part of the apparatus in FIG. 5.

Then, as shown in FIG. 5, a slide glass specimen 28A contained in a cassette 130A positioned selectively on the carrying pass is pushed out to the specimen receiving position 100 on the carrying pass by a lever (not shown) of the specimen delivery mechanism 120. That is, the slide feed lever 24A operates when a solenoid 108 is turned on and pushes a rod on a nose of the solenoid 108 upward. The solenoid 108 is turned off after the specimen slide 28A is pushed out to position 100, and thereafter the actuating rod returns to the home position. The slide feed lever 24A also returns simultaneously.

The carrier for carrying the specimen on the carrying pass has a slider 23 and feed levers 24A, 24B and makes a rectilinear motion with the shafts 25A, 25B as a guide. A pulley 214B is formed coaxially with a motor 212, and a turning force of the motor 212 is given to a pulley 214A through a wire 213.

Since the wire 213 and the moving slider 23 are coupled with each other, the turning force of the motor is transferred to the carrier.

The specimen replacing position 200 is the one for extracting the specimen slide 28A delivered by the slide feed levers 24A, 24B to the measuring part 400 comprising the microscope and the stage. The measuring part 400 classifies and measures the specimen slide 28A after it is adsorbed (picked up) and moved by the holding arms 16A, 16B.

The specimen holding position 300 is arranged on an almost straight extension connecting the cassette 130A of the specimen feeder 150 and the specimen replacing position 200. If it is necessary to inspect a specimen that is not contained in cassette 130A, then the specimen, such as specimen 28D is placed in a specimen receiver 310. The specimen receiver 310 is constructed to be shiftable to the specimen holding position 300 through manual operation. The carrier 250 is used for moving specimen 28D to the specimen replacing position by movement of the slide feed levers 24A, 24B. Reference characters 218A, 218B, 218C denote position detectors for detecting positions of the slide feed levers 24A, 24B.

A function of the specimen carrier will be described next.

After the specimen 28A with a blood smeared on a slide glass is pushed out to the receiving position 100, the wire 213 moves by operation of the motor 212. The slider 23 then makes a rectilinear motion in harmony therewith, and the specimen slide 28A is delivered to the measuring part extraction port position 200 and adsorbed to the measuring part 400. During operation for classifying the specimen slide 28A, the slide feed levers 24A, 24B return again to the specimen receiving position 100 to receive the specimen slide 28B and start shifting likewise. However, the specimen slide 28B is carried to the specimen holding position 300, past the measuring part extraction port position 200 and is then kept waiting until the classification measuring work of the specimen slide 28A is over.

After the work is over, since the specimen slide 28A is returned to the measuring part outlet position 200 from the measuring part 400, the waiting specimen slide 28B is fed leftward by the slide feed lever 24B, and while the specimen slide 28A returned to the measuring part extraction port position is fed leftward by the lever 24A, the specimen 28B is stopped at the measuring part outlet position 200. Then, while the specimen slide 28B is picked up by the measuring part 400 for the classifying work, the first specimen slide 28A is pushed to shift it to a specimen containing position on the left end. Thus, the specimen slide 28A is returned to be contained in the cassette 130A which is the cassette from which the specimen slide 28A was extracted. After the specimen slide 28A is contained in the cassette 130A, the slide feed levers 24A, 24B shift to the specimen receiving position 100 to receive the next specimen slide, namely a third specimen slide 28C.

The specimen 28C is shifted to the specimen holding position 300, retained there for waiting until observation of the previous specimen 28B through the microscope comes to an end.

The specimen slides can be replaced smoothly by repeating the above-described operation in sequence.

Figure 2:
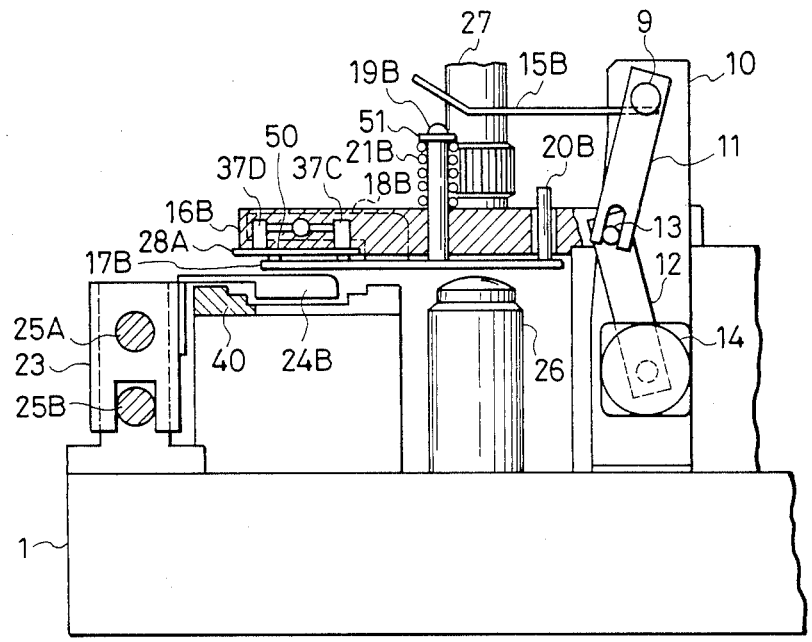
FIG. 2 is a schematic side view, partly in section and cutaway, showing the apparatus of FIG. 1 from right.

Next, a function of the measuring apparatus 400 will be described with reference to FIG. 3. An observation position of the microscope is formed between the condenser lens 26 and the objective 27 as shown in FIG. 1 and FIG. 2. When observation of the slide specimen 28A held on the holding arms 16A, 16B is over, the specimen 28A is placed on the specimen replacing position 200 on the rail 40 according to a motion of the X—Y stage 2 as shown in FIG. 1 and FIG. 2 during the "REPLACING POSITION" segment indicated in the graph of FIG. 3 for X—Y stage 2.

Figure 3:
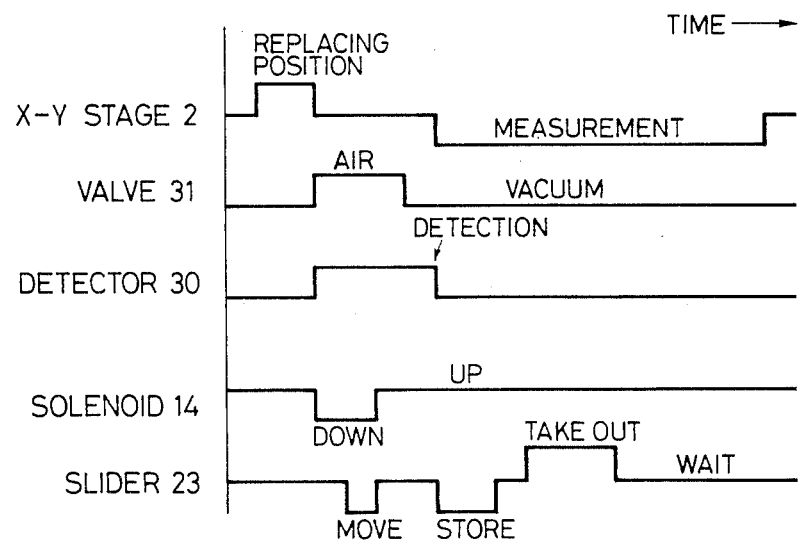
FIG. 3 is a timing chart of operation of the apparatus of FIG. 1.

Whenever the slide specimen 28A comes to the replacing position, the three-way directional control solenoid valve 31 shown in FIG. 4 operates to shut off vacuum pressure in the tube 33 to atmospheric pressure, as indicated by the "AIR" segment of the graph of FIG. 3 for valve 31 therefore the slide specimen 28A held at the reference plane of the lower surface of the specimen holding arm 16 is released.

On the other hand, when the rotary solenoid 14 rotates synchronously with an electrical signal to control is the three-way direction control solenoid valve 31, (during the "DOWN" segment of the graph of FIG. 3 for detector 30) the slide shafts 19A, 19B right under the push plates 15A, 15B are depressed by the push plates. Therefore the specimen retainers 17A, 17B also descend, and the slide specimen 28A is dropped into a groove of the rail 40. The specimen retainers 17A, 17B pass notches of the rail 40 to come down to a position lower than the rail 40. The slider 23 is driven by the pulse motor 212. When the slider 23 shifts leftward, (during the "MOVE" cycle of slider 23 as indicated in FIG. 3) the slide specimen 28A having dropped onto the rail 40 is pushed by the left side lever 24A to shift it leftward. The next slide specimen 28B waiting between the levers 24A, 24B stops at the specimen replacing position 200 at the end of the "MOVE" cycle. At this point of time the rotary solenoid 14 is turned off by the electrical signal, (as indicated by the "UP" portion of the solenoid 14 line in FIG. 3) and the push plates 15A, 15B also reset. Therefore, the specimen retainers 17A, 17B also ascend with the slide specimen 28B placed thereon on the force of springs 21A, 21B, and the slide specimen 28B is picked up by the vacuum adsorption surface of the holding arms 16A, 16B. When the slide specimen 28B is held on the lower surface of the specimen holding arm 16 at a constant position in both directions X and Y by a positioning mechanism (not indicated in the drawing), the three-way directional control solenoid valve 31 is turned on, and the slide specimen 28B is picked up by vacuum (as indicated by the leading edge of the "VACUUM" cycle of valve 31 in FIG. 3). When a specified vacuum pressure is detected by the vacuum pressure detector 30, (during the "DETECTION" cycle of detector 30) the X—Y stage 2 is driven, and the slide specimen 28B is observed and measured (during the "MEASUREMENT" cycle of X—Y stage as shown in FIG. 3) at an analysis scanning position under the microscope.

The slide specimen 28A having been measured completely is contained in a cassette of the containing part according to an operation of the slider 23 (during a "STORE" duration of the cycle of slider 23), and the next slide specimen 28C is drawn out and carried to the specimen holding position for waiting (during a "TAKE OUT" duration of the cycle shown in FIG. 3 for slider 23). When the specimen reaches the holding position the slider goes through a "WAIT" portion of its cycle as indicated in FIG. 3. Since oil on the slide specimen is absorbed by the vacuum suction, the oil tank 29 is for storing the oil so that it does not to flow electric parts such as the vacuum pressure detector 30 and others.

While the above-described operation is repeated, there may be warped slide specimens present among a multiplicity of specimens as mentioned hereinbefore. Such slide specimens cannot be corrected for warp. Air is capable of leaking in unavoidably. Air leaks where the vacuum adsorption surface 50 is flawed. Further, the air leaks where the slide specimen is damaged. The air also leaks in the case when the slide specimen is not set in duly for defective replacement. The air may leak due to gas, dust and the like which are smeared on the surface of the slide specimen to be absorbed. Thus, various causes may be the reason for air leakage, however, the air leakage due to flaws or other defects of the vacuum adsorption surface 50 arises whenever a specimen is inspected and measured, but the air leakage due to a warp of the slide specimen, gas, dust and the like arises at the time of inspection only. Accordingly, the situation in which the air leaks and thus a normal vacuum pressure is not obtained through inspections will be detected on the vacuum pressure detector 30 and controlled by a control circuit 34 and a computer 35. Then it can be determined whether the specimen holding arm 16 or the slide specimen 28 is defective. In this embodiment, an inspection is specified to be repeated three time consecutively, and the apparatus will be stopped for infeasibility of analysis scanning at the fourth inspection.

Then, a clearance between the slide specimen and the objective at the analysis scanning position is limited to several microns, therefore the specimen shifted to the analysis scanning position with large dust or the like left thereon is capable of damaging the objective. Accordingly, the vacuum pressure detector 30 having the vacuum pressure specified to a moderate range will be efficient enough to detect the size of a flaw on the arm, the size of dust on the slide specimen or defective insertion thereof.

We claim:

1. In a specimen inspection apparatus provided with:
   a movable holder means (440) for holding a specimen by vacuum adsorption;
   a microscope (400, 26, 27) for observing therethrough the specimen held by said holder means;
   a means (250) for carrying the specimen to be delivered to said holder means so as to place it in a specimen replacing position (200);
   the improvement comprising;
   specimen holding arm means (16,) provided on said holder means, said specimen holding arm means having a vacuum adsorption surface (50) capable of coming in contact with a surface of the specimen;
   means (17, 19, 21) for pushing said specimen elastically toward said vacuum adsorption surface while the specimen is observed through said microscope.

2. The specimen inspection apparatus as defined in claim 1, comprising means (11, 12, 13, 14, 15) for moving said elastically pushing means in the direction detached from said vacuum adsorption surface side while said specimen holding arm means are kept on said specimen replacing position.

3. The specimen inspection apparatus as defined in claim 1 or claim 2, said elastically pushing means having a means (18) for detaching the specimen mechanically from said vacuum adsorption surface.

4. The specimen inspection apparatus as defined in claim 1, comprising means (30, 34, 35) for deciding whether or not a vacuum adsorption state is good while said specimen holding arm means hold the specimen.

5. The specimen inspection apparatus as defined in claim 1, wherein said carrying means is provided with a carrying pass and carrier means (23, 24) for shifting a position of the specimen on the carrying pass, said carrier means retaining the next specimen at a waiting position (300) when the previous specimen in observed through said microscope and then shifting said next specimen to said specimen replacing position (200) from said waiting position after said previous specimen has been observed completely.

6. The specimen inspection apparatus as defined in claim 5, said carrier means having a plurality of lever means (24A, 24B) capable of shifting a plurality of specimens concurrently.

7. In a specimen inspection apparatus provided with a holder means for holding a specimen by vacuum adsorption, a microscope for observing therethrough the specimen held on said holder means, a means for carrying the specimen to be delivered to said holder means so as to place it in a specimen replacing position;
   the improvement comprising a specimen holding arm means within said holder means, said specimen holding arm means having a pair of holding arms with a vacuum adsorption surface capable of coming in contact with a surface of the specimen formed thereon and also having a pair of auxiliary means (17, 18, 19, 21) for bringing the specimen into contact with or detaching it from said vacuum adsorption surface.

* * * * *